Figure 1:
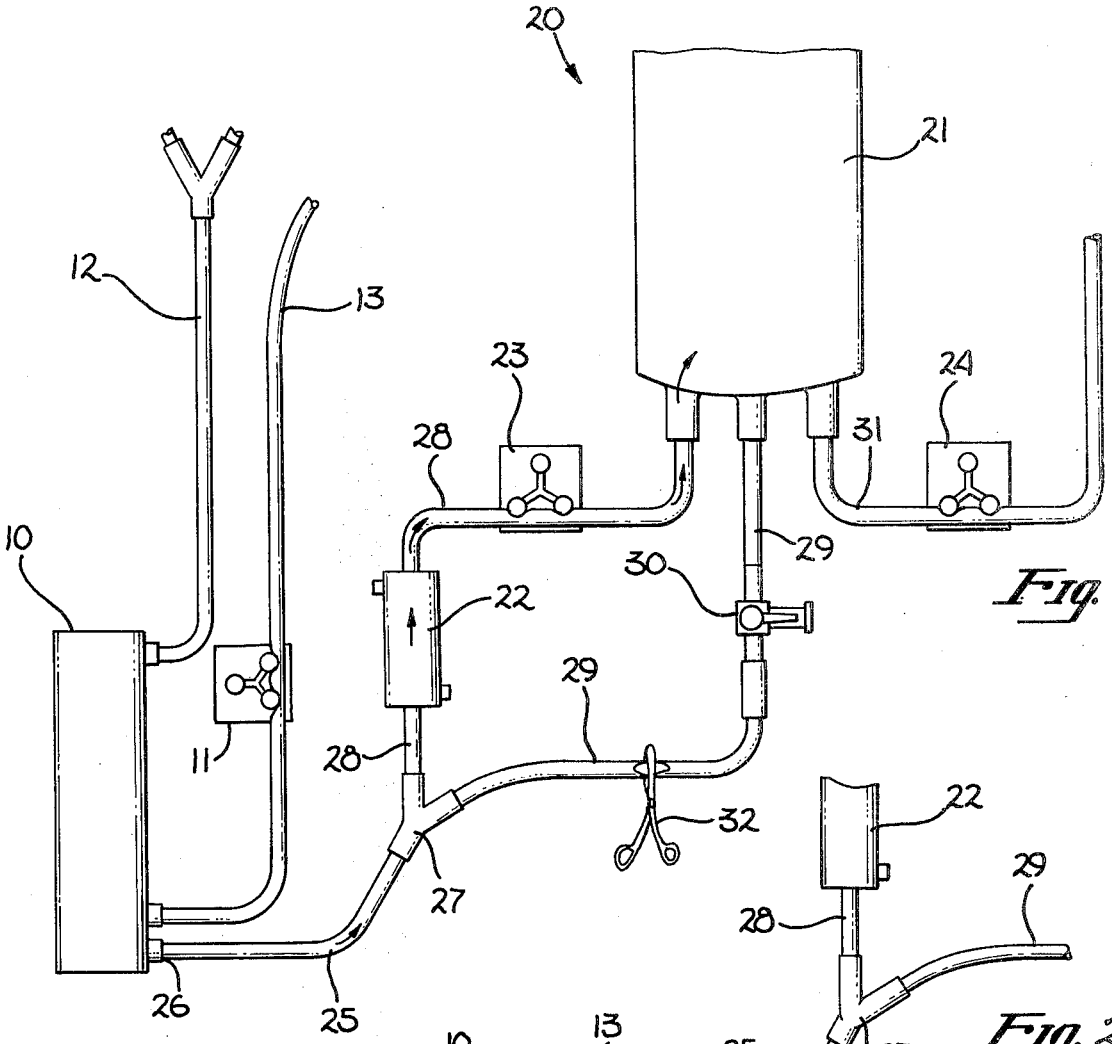
Figure 2:
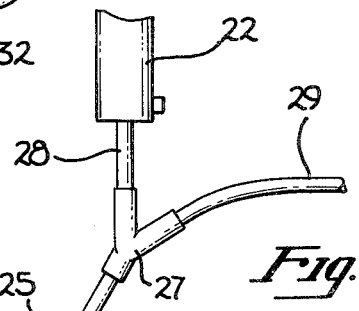
Figure 3:
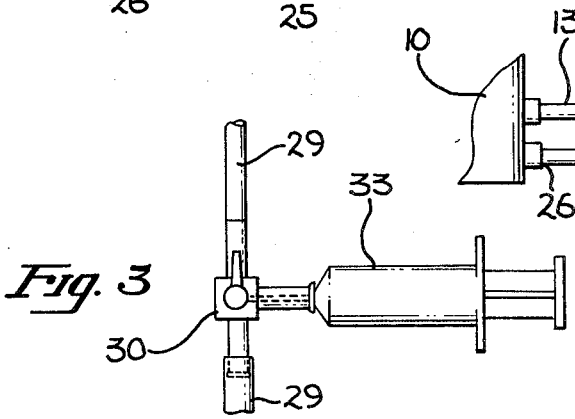
Figure 4:
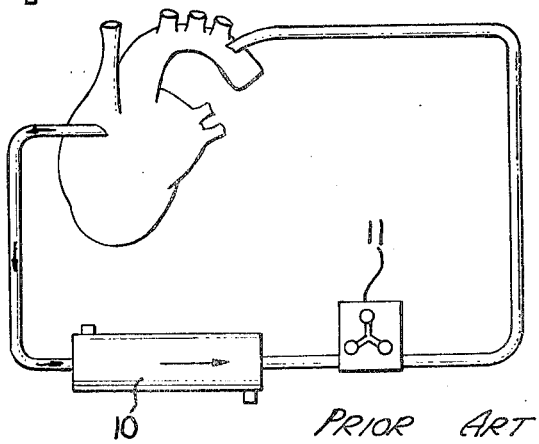
Fig. 4 PRIOR ART

United States Defensive Publication [19] (H) [11] T994,001

Buckberg et al. [43] May 6, 1980

[54] HYPOTHERMIC CARDIOPLEGIA ADMINISTRATION SET

[76] Inventors: Gerald D. Buckberg, 13238 Riviera Ranch Rd., Los Angeles, Calif. 90049; Charles W. Dyson, 1734 S. Westgate Ave., Los Angeles, Calif. 90025

[21] Appl. No.: 918,799

[22] Filed: Jun. 26, 1978

[51] Int. Cl.[2] ..... A61M 5/00

[52] U.S. Cl. ..... 128/214 R; 128/214 A; 128/214 D; 128/214.2; 128/DIG. 3

[57] ABSTRACT

The invention is an improved delivery system for injecting a cardioplegic solution made mostly of a patient's own blood into his heart in order to arrest it. The delivery system is used in combination with a cardiopulmonary bypass apparatus which includes an oxygenator, a roller pump, and typing connecting the patient's heart to the oxygenator so that patient's blood will flow into the oxygenator and the roller pump will pump it out of the oxygenator back into the patient's heart. The delivery system includes a blood bag for storing a portion of the patient's blood, a Y-shaped tubing having a first end with a single opening and a second end with a pair of openings with the single end mechanically coupled to the oxygenator so that the blood will travel from the oxygenator into the Y-shaped tubing, and a heat exchanger disposed between the blood bag and one of the pair of openings of the second end of the Y-shaped tubing and connected thereto so that blood may be pumped from the oxygenator through the heat exchanger into the blood bag by a first small roller pump. The delivery system also includes a stopcock which is connected to the other opening at the second end of the Y-shaped tubing and is also connected to the blood bag so that drugs may be injected into the patient's blood in the blood bag in order to form the cardioplegic solution through the stopcock. A clamping device is used to first clamp off second opening of the Y-shaped tubing and then to clamp off first end thereof. There is also an output tubing and a second small roller pump for pumping the cardioplegic solution into the heart in order to arrest it.

1 Claim, 1 Sheet Drawing,

16 Pages Specification

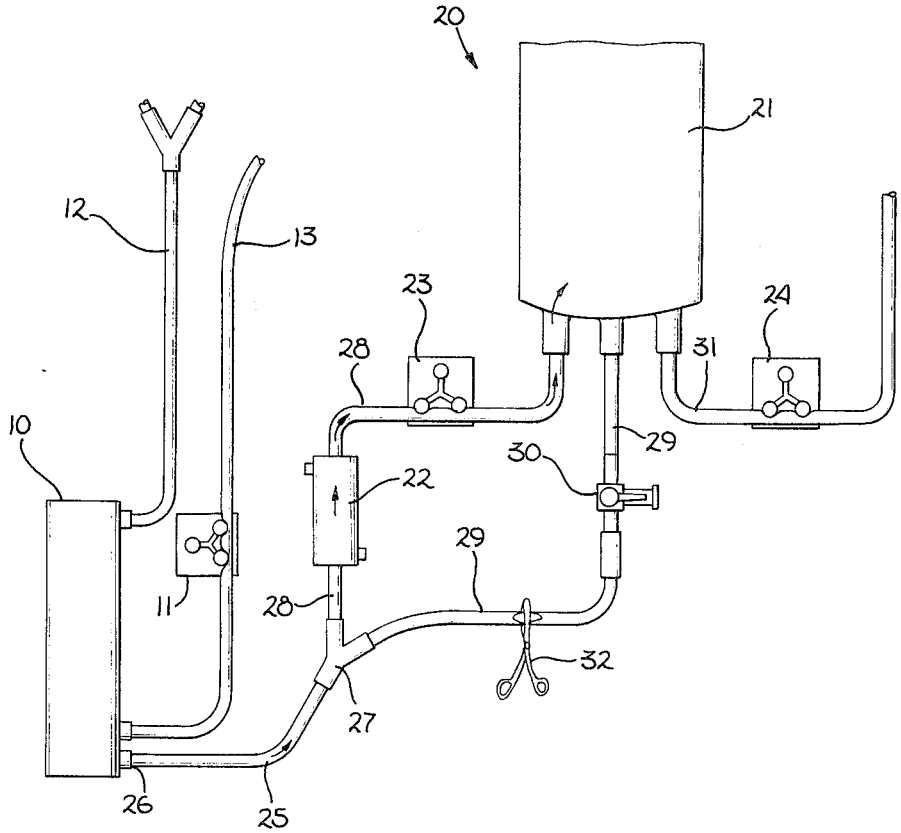

The file of this unexamined application may be inspected and copies thereof may be purchased (849 O.G. 1221, Apr. 9, 1968).